(12) United States Patent
Dermody et al.

(10) Patent No.: US 8,033,164 B2
(45) Date of Patent: Oct. 11, 2011

(54) CORROSION TESTING APPARATUS AND METHOD

(75) Inventors: Daniel L. Dermody, Midland, MI (US); Keith Harris, Midland, MI (US); David A. Hayes, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 464 days.

(21) Appl. No.: 12/334,760

(22) Filed: Dec. 15, 2008

(65) Prior Publication Data

US 2009/0158827 A1    Jun. 25, 2009

Related U.S. Application Data

(60) Provisional application No. 61/015,417, filed on Dec. 20, 2007.

(51) Int. Cl.
*G01N 17/00* (2006.01)
(52) U.S. Cl. .................................. 73/86; 73/87; 422/53
(58) Field of Classification Search ......... 73/86; 422/53
See application file for complete search history.

(56) References Cited

U.S. PATENT DOCUMENTS

| | | | |
|---|---|---|---|
| 6,365,034 B1 * | 4/2002 | Spellane | 205/775.5 |
| 6,792,357 B2 * | 9/2004 | Menon et al. | 702/27 |
| 7,131,335 B2 * | 11/2006 | Textor | 73/716 |
| 2006/0189963 A1 * | 8/2006 | Richards et al. | 604/891.1 |

OTHER PUBLICATIONS

Dewan et al., "Corrosion at Metal Interfaces A Study of Corrosion Rate and Solution Properties, Including Electrical Conductance, Viscosity, and Density", Industrial & Engineering Chemistry Research, 2002, 914-921, American Chemical Society Publications.
"Corrosion Monitoring", Pepperl+Fuchs, 2002.
"Mobil Stern Tube Lubricant", Exxon-Mobil Marine Ltd., Surrey, United Kingdom, 2007.

* cited by examiner

*Primary Examiner* — Lisa M Caputo
*Assistant Examiner* — Jamel Williams (57) ABSTRACT

The present invention relates to an apparatus and method as described in the specification and drawings for parallel high throughput corrosion testing and electroplating testing of test coupons.

10 Claims, 2 Drawing Sheets

CORROSION TESTING APPARATUS AND METHOD

CROSS-REFERENCE TO RELATED APPLICATION(S)

The present application claims benefit from U.S. Provisional Patent Application No. 61/015,417, filed Dec. 20, 2007, which U.S. provisional patent application is hereby incorporated by reference in its entirety.

FIELD OF THE INVENTION

The present invention generally relates to an apparatus and method for parallel high throughput corrosion testing and electroplating testing of test coupons.

BACKGROUND OF THE INVENTION

Corrosion testing is used to detect performance flaws in, and electroplating testing is used to find improvements in performance of, an industrial material such as, for example, a metal, a plastic, and a glass. For instance, testing corrosion of metals is important for ensuring safe functioning and long-term physical stability of manufactured items and structures such as, for example, aircraft, automobiles, bridges, metal-frame buildings, ships, trucks, and aerosol cans. Thus, it is important to test for potential corrosive effects of industrial fluids such as, for example, airplane deicing fluids and ship stern lubricants that come into contact with these manufactured items or structures before the industrial fluids are employed in industry. An accepted method for testing corrosion performance of metals with ship stern lubricants is ASTM D665, "Standard Test Method for Rust-Preventing Characteristics of Inhibited Mineral Oil in the Presence of Water" (ASTM International, Conshohocken, Pa., USA). Each corrosion test using this method requires a separate metal coupon and about 300 milliliters of a test liquid. Components of the test liquid may include water, an electrolyte such as sodium chloride, a ship stern lubricant, and, optionally, an additive such as a corrosion inhibitor. After testing, the metal coupon is visually inspected for evidence of corrosion such as pitting, cracking, and discoloration. There is a need for higher testing productivity and lower expense in the corrosion and electroplating testing arts.

SUMMARY OF THE INVENTION

A first embodiment of the invention is an apparatus comprising:
(a) a first test coupon, which comprises a top face and a bottom face;
(b) a test framework, which comprises a top face, bottom face, and a plurality of walls that define a number N of test holes; wherein the top and bottom faces of the test framework are generally flat, spaced apart from, and generally parallel to, each other; the test holes pass through the test framework between bottom openings at the bottom face of the test framework and top openings at the top face of the test framework and are spaced apart from each other; N is an integer of from 2 to 200; and the bottom face of the test framework operatively contacts, around the bottom openings of at least two of the test holes, the top face of the first test coupon to independently circumscribe at least two separate test areas on the top face of the first test coupon; and
(c) a second test coupon, which comprises a top face and a bottom face; wherein the top face of the test framework operatively contacts, around the top openings of the at least two test holes, the bottom face of the second test coupon to independently circumscribe at least two separate test areas on the bottom face of the second test coupon;

wherein at least two test chambers are defined by the walls of the at least two test holes, the at least two separate test areas circumscribed on the top face of the first test coupon, and the at least two separate test areas circumscribed on the bottom face of the second test coupon.

A second embodiment of the invention is a method comprising:
(a) in an apparatus of the first embodiment, contacting a corrosion testing amount of a test liquid in each one of the at least two test chambers to at least one of the first and second test coupons, wherein the test liquids in the at least two test chambers may be the same or different and are secured against fluid communication with each other; and
(b) analyzing at least one of the first and second test coupons for corrosion.

Additional embodiments are described in accompanying drawings and the remainder of the specification.

DETAILED DESCRIPTION OF THE INVENTION

The present invention is summarized above and further described below. The invention apparatus and process may be used for testing electroplating of a substrate by a metal and for testing for different types of corrosion such as, for example, chemical, electrochemical, microbial, and voltaic corrosion.

In describing the present invention, certain abbreviations, phrases, terms, and words are used that are defined here. When interpreting a meaning of an abbreviation, phrase, term, or word, its definition here governs unless, for a particular use, a different meaning is stated elsewhere in this specification or unless a context of the use of the abbreviation, phrase, term, or word clearly indicates a different meaning is intended from the definitions provided here.

Highlighted Abbreviations

ASTM—American Society for Testing and Materials
° C.—degrees Celsius
mL—milliliter(s)
NaCl—sodium chloride
%—percent
$S \cdot m^{-1}$—siemens per meter
μL—microliter(s)

Articles "a" and "an" refer to singular and plural forms of what is being modified by the articles. The term "or" refers to members in a list either singly or in any combination.

The term "comprising," which is synonymous with the terms "including," "containing," "having," and "characterized by," is inclusive or open-ended. Likewise, the term "group of" is also open-ended. These terms do not exclude additional elements, materials, ingredients, or method steps, including unrecited ones, even if the additional elements, materials, ingredients, or method steps are present in major amounts. When the term "comprising" is used as a transition from a claim's preamble to the claim's body (i.e., as a transitional term), the entire claim is open-ended.

The phrases "consisting of" or "group consisting of" are closed terms. These phrases exclude any element, step, or ingredient not specified. When the phrase "consisting of" is used as a transitional phrase in a claim, the phrase closes the claim to the inclusion of materials, elements, or steps that are not specifically recited in the claim except for impurities ordinarily associated therewith and materials, elements or steps that are unrelated to the claimed invention. When the phrase "consisting of" is used in a clause of the body of the claim rather than immediately following the preamble, it limits only the element, step, or material set forth in that clause and other elements, materials, or steps outside of the clause are not excluded from the claim. The present invention also includes embodiments written by modifying the "comprising" embodiments described elsewhere herein by replacing the transitional term "comprising" with the transitional phrase "consisting of."

The phrase "consisting essentially of" may be used in a claim's preamble to limit the scope of the claim to the specified materials, elements, or steps and those that do not materially affect the basic and novel characteristic or characteristics of the claimed invention. Referring to preambles, a "consisting essentially of" claim occupies a middle ground between closed claims that are written in "consisting of" format and fully open claims that are drafted in a "comprising" format. The present invention also includes embodiments written by modifying the "comprising" embodiments described elsewhere herein by replacing the transitional term "comprising" with the transitional phrase "consisting essentially of."

Figure 1:
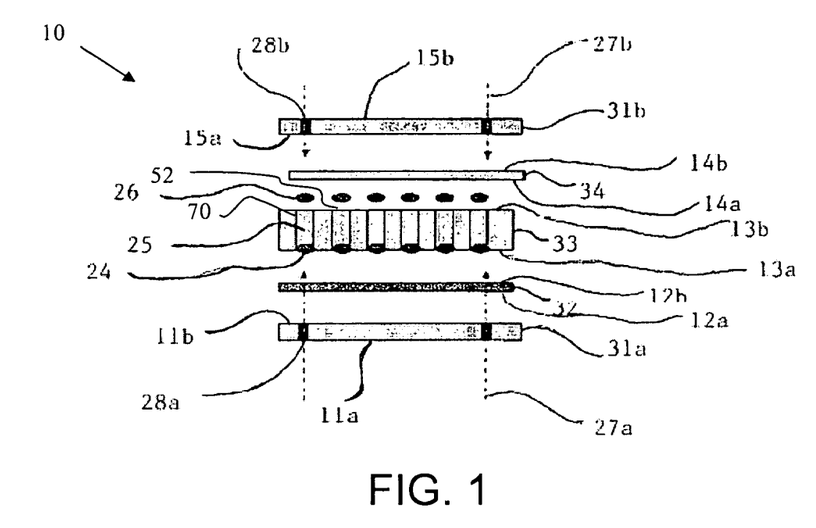
FIG. 1 is an exploded view of an embodiment of an invention apparatus (externally screw-threaded fasteners 92 and 94 are not shown).

An embodiment of the invention apparatus 10 is illustrated in an exploded view in FIG. 1. In invention apparatus 10 of FIG. 1, there is first backing means 31a having a bottom face 11a and a top face 11b. There is a first test coupon 32 (e.g., an ASTM standard steel coupon) having a bottom face 12a and a top face 12b. Also, there are forty-eight O-rings 24 (six of which are shown in FIG. 1) and forty-eight additional O-rings 26 (six of which are shown in FIG. 1), the O-rings being comprised of, for example, a fluoroelastomer. There is a test framework 33 (e.g., comprised of polyetheretherketone (PEEK)) having a bottom face 13a, a top face 13b, and walls 70 defining forty-eight flanged test holes 25 (six of which are shown in FIG. 1), which are arranged in a rectangular shaped grid (not visible) comprising eight rows designated A to H along its width (i.e., back to front) by six columns designated 1 to 6 along its length (i.e., left to right). Thus, the forty-eight test holes 25 are given location designations A1 to A6, B1 to B6, etc. through H1 to H6. Test holes 25 that pass through (i.e., traverse) test framework 33 between bottom openings 51 (not indicated) at bottom face 13a of test framework 33 and top openings 52 at top face 13b of test framework 33. Bottom openings 51 (not indicated) are in contact with O-rings 24. There is a second test coupon 34 (e.g., a copper coupon) having a bottom face 14a and a top face 14b and a second backing means 31b having a bottom face 15a and a top face 15b. There are eight perimeter holes 28a in a perimeter apron 38 (not indicated) of first backing means 31a and eight perimeter holes 28b in a perimeter apron 39 (not indicated) of second backing means 31b. There is one center fastening hole 91, 95, 81, 83, and 85 (all not indicated) in each of first and second backing means 31a and 31b, first test coupon 32, second test coupon 34, and test framework 33, respectively. There are eighteen externally screw-threaded fasteners comprising two center fasteners 92 (not shown) and sixteen perimeter fasteners 94 (not shown). Each one of the eighteen externally screw-threaded fasteners 92 and 94 threadably engages a different one of the internally screw-threaded holes 28a and 91, and 28b and 95, in first and second backing means 31a and 31b, respectively. One center fastener 92 sequentially threadably engages center holes 91, 81, and 85 of first backing means 31a, first test coupon 32, and test framework 33, respectively. The other center fastener 92 sequentially threadably engages center holes 95, 83, and 85 of second backing means 31b, second test coupon 34, and test framework 33, respectively. Arrows 27a indicate directions of travel of nine of the eighteen externally screw-threaded fasteners (one center fastener 92 and eight perimeter fasteners 94, all not shown) through the one center fastening hole 91 (not indicated) and the eight fastening holes 28a in the perimeter apron 38 (not indicated) of the first backing means 31a and arrows 27b indicate directions of travel of nine of the eighteen externally screw-threaded fasteners (one center fastener 92 and eight perimeter fasteners 94, all not shown) through the center fastening hole 95 (not indicated) and eight fastening holes 28b in the perimeter apron 39 (not indicated) of the second backing means 31b. The arrows 27a and 27b also indicate the directions of opposing compression forces operatively applied by the externally screw-threaded fasteners 92 and 94 (all not shown) and first and second backing means 31a and 31b to the first test coupon 32 and second test coupon 34, respectively, and, in turn, to O-rings 24 and 26, respectively, and bottom face 13a and top face 13b, respectively, of test framework 33. Test chambers 55 (not indicated in exploded view of FIG. 1) are defined by walls 70 of test holes 25 and areas 44 (not indicated) circumscribed by O-rings 24 on top face 12b of first test coupon 32 and areas 46 (not indicated) circumscribed by O-rings 26 on bottom face 14a of second test coupon 34.

Again referring to FIG. 1, the widths (front to back) and lengths (left to right) of the first test coupon 32, the second test coupon 34, and test framework 33 are about the same. Not indicated, the first and second backing means 31a and 31b are wider and longer than the first test coupon 32, the second test coupon 34, and test framework 33, thereby providing perimeter aprons 38 and 39 (not indicated) of first and second backing means 31a and 31b, respectively. Top face 11b of first backing means 31a operatively contacts the bottom face 12a of first test coupon 32. The top face 12b of first test coupon 32 operatively contacts the O-rings 24, which in turn operatively contact bottom face 13a at the flanged test holes 25 of test framework 33. A top face 13b of test framework 33 operatively contacts O-rings 26 at the flanged test holes 25 of test framework 33 and, in turn, O-rings 26 operatively contact a bottom face 14a of second test coupon 34. A top face 14b of second test coupon 34 operatively contacts a bottom face 15a of second backing means 31b.

Again referring to FIG. 1, the center fastening holes 91 and 95 (both not indicated) in first and second backing means 31a and 31b, respectively, and center holes 81, 83, and 85 in first test coupon 32, second test coupon 34, and test framework 33, respectively, are all aligned with each other to threadably engage center fasteners 92. Perimeter aprons 38 and 39 (both not indicated) in each of first and second backing means 31a and 31b, respectively, extend beyond the first test coupon 32, second test coupon 34, and test framework 33. A first eight perimeter fasteners 94 (not shown) pass through eight internally screw-threaded fastening holes 28a in the perimeter apron area 38 (not indicated) of first backing means 31a in an upward vertical direction indicated by arrow 27*a* and a second eight perimeter fasteners 94 (not shown) pass through eight internally screw-threaded fastening holes 28*b* in the perimeter apron area 39 (not indicated) of second backing means 31*b* in a downward vertical direction indicated by arrow 27*b*. The eight internally screw-threaded fastening holes 28*a* and eight internally screw-threaded fastening holes 28*b* are positioned so that the first eight perimeter fasteners 94 (not shown) and second eight perimeter fasteners 94 (not shown) do not penetrate the first test coupon 32, the second test coupon 34, or test framework 33, but instead abut and directly contact outer edges (not indicated) of the first test coupon 32, the second test coupon 34, and test framework 33. One center fastener 92 (not shown) passes through the center fastening holes 91 and 81 (both not indicated) of first backing means 31*a* and first test coupon 32, respectively, and into the center fastening hole 85 (not indicated) of test framework 33 in an upward vertical direction indicated by arrow 27*a*. The other center fastener 92 (not shown) passes through the center fastening holes 95 and 83 (both not indicated) of second backing means 31*b* and second test coupon 34, respectively, and into the center fastening hole 85 (not indicated) of test framework 33 in an downward vertical direction indicated by arrow 27*b*. The eighteen fasteners 92 and 94 (all not shown) are tightened in the perimeter fastening holes 28*a* and 28*b* and center fastening holes 91, 81, and 85 and 95, 83, and 85 (all not indicated) in an order designed to avoid deforming the first test coupon 32 and second test coupon 34.

Again referring to FIG. 1, when invention apparatus 10 is unassembled (e.g., for cleaning), test holes 25 are in fluid communication with bottom face 13*a* and top face 13*b* of test framework 33. When invention apparatus 10 is assembled as described above, test chambers 55 (not indicated in exploded view of FIG. 1)), which are defined by walls 70 of test holes 25, areas 44 (not indicated) circumscribed by O-rings 24 on top face 12*b* of first test coupon 32 and areas 46 (not indicated) circumscribed by O-rings 26 on bottom face 14*a* of second test coupon 34, are sealed against fluid communication with each other.

While invention apparatus 10 in FIG. 1 comprises forty-eight test chambers 55, more preferred is invention apparatus 100 (not shown) having a ninety-six test chambers 155, wherein invention apparatus 100 is constructed and assembled in a manner that is directly analogous to construction and assembly of invention apparatus 10 of FIG. 1 described above. Thus, invention apparatus 100 (not shown) is comprised of first backing means 131*a* having a perimeter apron 138, bottom face 111*a* and top face 111*b* and a center fastening hole 191 and eight perimeter fastening holes 128*a* therebetween; second backing means 131*b* having a perimeter apron 139, bottom face 115*a* and top face 115*b* and a center fastening hole 191 and eight perimeter fastening holes 128*b* therebetween; first test coupon 132 having bottom face 112*a* and top face 112*b* and a center fastening hole 181 therebetween; second test coupon 134 having bottom face 114*a* and top face 114*b* and a center fastening hole 183 therebetween; test framework 133 having bottom face 113*a*, top face 113*b* and a center fastening hole 185 therebetween, and having walls 170 defining ninety-six test holes 125, wherein each test hole 125 has a bottom opening 151 in bottom face 113*a* and a top opening 152 in top face 113*b*; ninety-six O-rings 124; ninety-six O-rings 126; two externally screw-threaded fasteners 192; and sixteen externally screw-threaded fasteners 194; all not shown. Ninety-six test chambers 155 being disposed in invention apparatus 100 and defined by walls 170 of test holes 125, areas 144 circumscribed by O-rings 124 on top face 112*b* of first test coupon 132 and areas 146 circumscribed by O-rings 126 on bottom face 114*a* of second test coupon 134 (all not shown), wherein test chambers 155 are sealed against fluid communication with each other. See Examples 1 and 2 for use of an embodiment of ninety-six test chamber apparatus 100. In the description below, examples are illustrated with references to elements (e.g., first test coupon 32) of invention apparatus 10 of FIG. 1, but such references apply equally to corresponding elements (e.g., first test coupon 132, not shown) of invention apparatus 100 (not shown).

Figure 2:
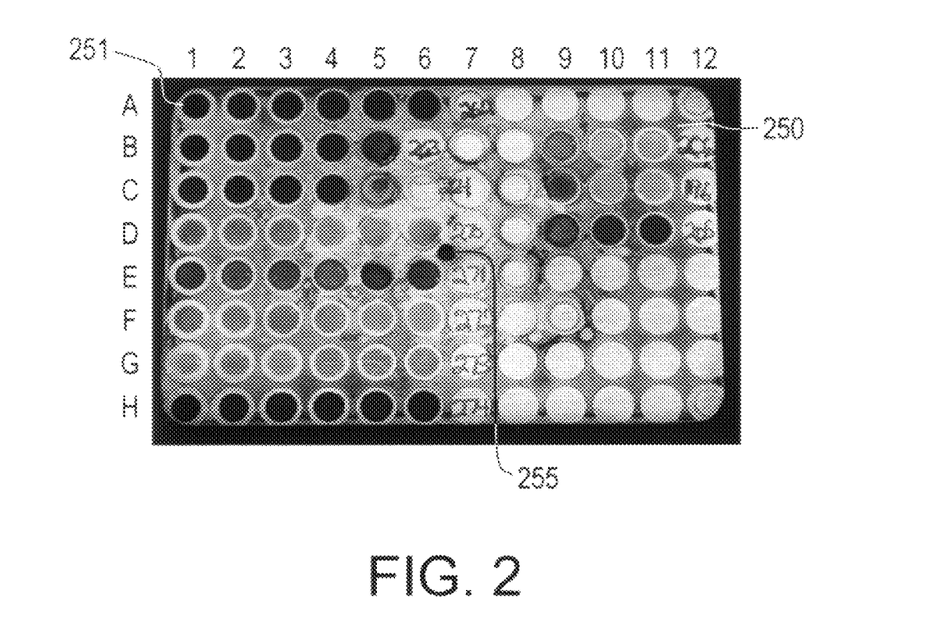
FIG. 2 is a black and white photograph of a steel coupon showing corrosion results from testing the steel coupon as described in Example 2.

FIG. 2 is a black-and-white photograph of steel test coupon 250 showing corrosion results from testing the steel coupon as described in Example 2. In FIG. 2, ninety-six round test areas 251 are shown in a grid comprising rows A to H and columns 1 to 12. A particular test area may be referenced by naming its row and column. For illustration, test area 251 at location A1 is identified in FIG. 2. Also, an unthreaded fastening hole 255 is visible in steel test coupon 250 between test areas 251 located at D6, D7, E6, and E7. See Example 2 for a detailed description of steel coupon 250.

The invention apparatus and method increases productivity of corrosion testing of test coupons from one corrosion test per test coupon to from 2 to 200 corrosion tests (or more) per test coupon. In other embodiments, from 4 to 144 corrosion tests are conducted with one test coupon. In still other embodiments, from 8 to 144; from 8 to 100; or from 16 to 96 corrosion tests are conducted with one test coupon.

As mentioned previously, the invention apparatus comprises, among other things, a test framework (e.g., 33). A "test framework" refers to a structural frame comprised of any chemical and corrosion resistant structural material such as, for example, ceramics, glass, polymers, and interpolymers. Preferably, the test framework (e.g., 33) is comprised of a polymer- or interpolymer-based chemical and corrosion resistant structural material. Preferred examples of polymer- and interpolymer-based chemical and corrosion resistant structural materials are polypropylene, polytetrafluoroethylene (PTFE), PTFE-g (glass-filled), polyetheretherketone (PEEK), polyoxymethylene (POM), POM (PTFE-filled), POM (glass-filled), polyphenylene oxide-POM copolymer, polyamide made from hexamethylene diamine and 1,12-dodecanedioic acid (PHDDA), a composite of PHDDA and a polyamide made from 1,4-phenylene-diamine and terephthaloyl chloride, polyvinylchloride (PVC), PVC (chlorinated), polycarbonate, and polycarbonate (glass-filled).

A test framework (e.g., 33) provides walls (e.g., 70) for test chambers (e.g., 55, not indicated) and spaces test coupons (e.g., 32 and 34) apart from each other. In some embodiments, a test framework (e.g., 33) is a generally rectangular-shape block having test holes (e.g., 25) that pass through (i.e., traverse) the test framework (e.g., 33) between bottom openings (e.g., 51, not indicated) at a bottom face (e.g., 13*a*) of the test framework (e.g., 33) and top openings (e.g., 52) at the top face (e.g., 13*b*) of the test framework (e.g., 33) and are spaced apart and generally parallel to each other. When not assembled in an invention apparatus (e.g., 10 of FIG. 1), the test holes (e.g., 25) are in fluid communication with the top face (e.g., 13*a*) and bottom face (e.g., 13*b*) of the test framework (e.g., 33).

In some embodiments, a test framework (e.g., 33), may comprise a securing test framework 33-*s*, which is a test framework that further functions in place of, or in addition to, a securing means 2 (not shown) to secure a first test coupon (e.g., 32), second test coupon (e.g., 34), or both, to the securing test framework 33-*s* such that, when both the first and second test coupons (e.g., 32 and 34) are secured to the securing test framework 33-*s* (with or without employing a separate securing means 2, not shown), test liquids (not shown) in the at least two test chambers (e.g., 55, not indicated) are not in fluid communication with each other. Examples of a securing test framework 33-*s* are a rectangular-shape block, wherein the rectangular-shape block further defines one or more slots or tabs above a top face (e.g., 13*b*) and below a bottom face (e.g., 13*a*) of the securing test framework 33-*s*, the one or more slots or tabs being dimensioned for snugly holding a test coupon (e.g., 32 and 34) against the top face or bottom face, respectively. Test coupons (e.g., 32 and 34) may be slid into and out of the slots or tabs.

Profiles of the test holes (e.g., 25) of the test framework (e.g., 33) may be any shape, but a generally circular profile, i.e., hollow right cylindrical with open ends, is typical. When its profile is circular, a test chamber (e.g., 55, not indicated) has a generally cylindrical shape. A profile of a test hole (e.g., 25) may be uniform or irregular and may or may not vary along a length of the test hole (e.g., 25) from the top face (e.g., 13*b*) to the bottom face (e.g., 13*a*) of the test framework (e.g., 33). A diameter of a test hole (e.g., 25) may be uniform or may vary along the length of the test hole (e.g., 25).

A test hole (e.g., 25) may be unflanged or flanged in a conventional manner at the top face (e.g., 13*b*), bottom face (e.g., 13*a*), or both of a test framework (e.g., 33). Such a flanged test hole (e.g., 25) is characterized by a flange or rim that is present at a shallow depth below the top face (e.g., 13*b*), bottom face (e.g., 13*a*), or both of the test framework (e.g., 33) that surrounds the flanged test hole (e.g., 25). The flange (i.e., the rim) is dimensioned for receiving an O-ring (e.g., 24). Other sealing means 4 (not shown, e.g., a gasket) may be used with a flanged test framework (e.g., 33).

Test holes (e.g., 25) may be positioned in any arrangement in a test framework (e.g., 33). Preferably, test holes (e.g., 25) are sufficiently spaced apart from each other such that structural integrity between reaction chambers (e.g., 55, not indicated) is maintained when first and second test coupons (e.g., 32 and 34, respectively) are secured to the test framework (e.g., 33). In some embodiments, the test holes (e.g., 25) are organized in an arrangement that mirrors an arrangement of wells in a conventional 96-well titer plate, e.g., in a grid comprising 8 rows and 12 columns.

As mentioned previously, the invention apparatus (e.g., 10 in FIG. 1) comprises, among other things, a test coupon (e.g., 32 and 34). A "test coupon" means a solid material that is studied for corrosion, electroplating, or both. A test coupon may be comprised of, for example, graphite, a metal, a metal alloy, a plastic, a glass, or a combination thereof (e.g., a laminate of a plastic on a metal or metal alloy). Corrosion includes galvanic corrosion (e.g., a rusting of a metal coupon), oxidative corrosion (e.g., oxidative degradation of a polymeric coating or organic coating on a ceramic substrate), dissolution testing (e.g., dissolution testing of a grease or wax on a metal for cleaning applications), or etch corrosion (e.g., an acid etching of glass). First and second test coupons (e.g., 32 and 34) may be the same or different.

A test coupon (e.g., 32 and 34) may be comprised of a material having a surface (e.g., 12*b*) of uniform composition that is exposed to a test liquid. A test coupon may have a uniform composition throughout (i.e., a uniform test coupon) or be comprised of a laminate of two or more layers (i.e., a laminate test coupon). A laminate test coupon is comprised of a testing layer and a substrate layer, wherein the testing layer is comprised of a material for corrosion or electroplating testing (e.g., a polymer, a glass, a metal or metal alloy) and the substrate layer is comprised of a support layer (e.g., a polymer, a glass, a metal or metal alloy), wherein the testing layer and the laminate layer are different (e.g., a gold testing layer on a carbon steel substrate layer). Further, a test coupon (e.g., 32 and 34) may be comprised of one, two or more parts, wherein each part may have a surface of uniform composition that is exposed to a test liquid, wherein the composition of the surfaces of the two or more parts of the multi-part test coupon may be the same or different. A test area on a surface of a multi-part test coupon may be of uniform composition or may overlap surfaces of two or more parts of the multi-part test coupon such that two or more different materials comprise the multi-part test coupon and are exposed to a same aliquot of a test liquid contained in one test chamber, thereby increasing productivity of the invention method. For example, in some embodiments, first and second test coupons (e.g., 32 and 34) are each independently comprised of one contiguous piece of metal. In other embodiments, at least one of the first and second test coupons is comprised of two or more separate pieces of the same or different metals, which may be placed side-by-side between a test framework (e.g., 33) and a backing means (e.g., 31*a* and 31*b*) to form at least a multi-part first test coupon 3 (not shown) and, optionally, a multi-part second test coupon 5 (not shown). For example, the invention apparatus may be comprised of a first multi-part test coupon (e.g., 3, not shown) that is actually half of a carbon steel coupon and half of a stainless carbon steel coupon, which may or may not touch each other, and a second multi-part test coupon (e.g., 5, not shown) is actually half of a copper coupon and half of a brass coupon, which may or may not touch each other. In such an apparatus, one or more test holes (e.g., 25) may be positioned at an interface between the half coupons for simultaneously testing corrosion of both coupons with the same aliquot of a test liquid. Preferably, however, each test area (e.g., 44 and 46) on a test coupon (e.g., 32 and 34) that a test hole (e.g., 25) circumscribes is of uniform composition (i.e., where a first test coupon comprises two or more separate pieces, the test area does not overlap the two or more separate pieces).

Test coupons (e.g., 32 and 34) may be any size, shape or thickness. In order to operatively contact a sealing means (e.g., 24 and 26) and prevent fluid communication between test chambers (e.g., 55, not indicated), the test coupon (e.g., 32 and 34) preferably is flat along portions of its face (e.g., 12*b* and 14*a*) that operatively contact the sealing means (e.g., 24 and 26) or test framework (e.g., 33). Conventional shapes of test coupons are round, rectangular (e.g., 32 and 34), or square. In some embodiments, the test coupons (e.g., 32 and 34) are a flat rectangular shape. Before corrosion testing, test coupons (e.g., 32 and 34) may be polished using a standard method according to ASTM International and one or more internally screw-threaded or unthreaded fastening holes (e.g., 81 and 83, not indicated) may be drilled through a test coupon (e.g., 32 and 34) (e.g., through the center) to facilitate securing the test coupon (e.g., 32 and 34) to at least one of the backing means (e.g., 31*a* and 31*b*), test framework (e.g., 33), or both.

A "metal test coupon" refers to a pure or alloy solid material composed of 60% by weight or more, preferably 70% by weight or more, of an unoxidized [i.e., a 0 oxidation state, e.g., Fe, i.e., Fe(0)] chemical element having one of the following atomic numbers: 4, 12 to 14, 21 to 32, 39 to 52, 56 to 60, 62 to 79, 82, 83, 89, and 90. The metal test coupon (e.g., 32 and 34) may consist essentially of the pure or alloy solid material or the metal test coupon may comprise a laminate metal test coupon. A laminate metal test coupon is comprised of a metal layer and a substrate layer, wherein the metal layer is comprised of pure or alloy solid material as described above and the substrate layer is comprised of a polymer, glass, or a different pure or alloy solid material. Examples of laminate metal test coupons are a metallized polymer or a coating of silver or gold on steel. Preferably, the layer of the pure or alloy solid of the laminate metal test coupon is what is being tested for corrosion. At least 90% by weight, preferably at least 95% by weight, more preferably at least 98% by weight, still more preferably at least 99.9% by weight of the metal test coupon, or the metal layer of the laminate metal test coupon is comprised of the pure or alloy solid material.

Composition of a metal test coupon (e.g., 32 and 34) is determined by a standard spectrochemical or chemical analysis method of ASTM International. Examples of the unoxidized chemical element that may comprise the composition of a metal test coupon are beryllium (Be), magnesium (Mg), aluminum (Al), silicone (Si), titanium (Ti), vanadium (V), chromium (Cr), manganese (Mn), iron (Fe), cobalt (Co), nickel (Ni), copper (Cu), zinc (Zn), gallium (Ga), germanium (Ge), zirconium (Zr), molybdenum (Mo), ruthenium (Ru), rhodium (Rh), palladium (Pd), silver (Ag), cadmium (Cd), indium (In), tin (Sn), tungsten (W), platinum (Pt), gold (Au), lead (Pb), and bismuth (Bi). First and second metal test coupons (e.g., 32 and 34) may be comprised of the same or different chemical element. Examples of suitable materials are recited later herein as members of a galvanic series. Some metal test coupons (e.g., 32 and 34) are commercially available from suppliers of metal test coupons for corrosion testing. Suppliers include Metal Samples Corrosion Monitoring Systems, a division of Alabama Specialty Products, Inc.

In some embodiments, a first test coupon comprises a first metal test coupon. In other embodiments, the first metal test coupon comprises palladium, platinum, gold, silver, titanium, stainless steel, silicon, brass, tungsten, tantalum, chromium, nickel, copper, carbon steel, lead, tin, aluminum, or zinc. In other embodiments, the first metal test coupon comprises titanium, stainless steel, silicon, brass, chromium, nickel, copper, or carbon steel. In other embodiments, the first test coupon comprises stainless steel or carbon steel.

In some embodiments, a second test coupon comprises a second metal test coupon. In other embodiments, the second metal test coupon comprises palladium, platinum, gold, silver, titanium, stainless steel, silicon, brass, tungsten, tantalum, chromium, nickel, copper, carbon steel, lead, tin, aluminum, or zinc. In other embodiments, the second test coupon comprises chromium, nickel, copper, or aluminum. In other embodiments, the second metal test coupon comprises copper or aluminum.

In some embodiments, first and second test coupons comprise a voltaic couple.

In another embodiment, the invention apparatus (e.g., 10 of FIG. 1) of the first embodiment further comprises at least one sealing means (e.g., 24 and 26), which either is disposed between, and forms a sealing contact with, the top face (e.g., 12b) of the first test coupon (e.g., 32) and the bottom face (e.g., 13a) of the test framework (e.g., 33) around a bottom opening of one of the at least two test holes (e.g., 25) or is disposed between, and forms a sealing contact with, the bottom face (e.g., 14a) of the second test coupon (e.g., 34) and the top face (e.g., 13b) of the test framework around a top opening of the same one of the at least two test holes (e.g., 25). A "sealing means" refers to any device having a bottom face (not indicated) and a top face (not indicated) that are generally parallel to, and spaced apart from, each other and that is useful for preventing fluid communication between test liquids in different test chambers (e.g., 55, not indicated) during a use of an invention apparatus in an invention method. An invention apparatus may employ no sealing means or one, preferably at least two, more preferably up to, and including, a multiple of 2 times the number N sealing means, wherein N is as defined previously.

In an invention apparatus having a sealing means (e.g., 24 and 26), a bottom face (not indicated) of the sealing means is in operative contact with a top face (e.g., 12b) of a first test coupon (e.g., 32) and a top face (not indicated) of the sealing means is in operative contact with a bottom face (e.g., 13a) of a test framework (e.g., 33) around a bottom opening (not indicated) of a test hole (e.g., 25) in the test framework (e.g., 33). Alternatively, a top face (not indicated) of the sealing means is in operative contact with a bottom face (e.g., 14a) of a second test coupon (e.g., 34) and a bottom face (not indicated) of the sealing means is in operative contact with a top face (e.g., 13b) of a test framework (e.g., 33) around a top opening (not indicated) of a test hole (e.g., 25) in the test framework (e.g., 33).

As mentioned before, an invention apparatus (e.g., 10 in FIG. 1) may employ a separate sealing means 2 (not shown); may not employ a separate sealing means 2 (not shown), but instead a test framework (e.g., 33) may also function as the sealing means 2 (not shown); or may employ a combination thereof. When there is more than one sealing means 2 (e.g., 24 and 26), each sealing means 2 (not shown) is comprised of the same or different material. Examples of separate sealing means 2 (not shown) are gaskets, O-rings (e.g., 24 and 26), waxes, and adhesives.

A "gasket" is a sheet-like framework comprised of any chemical and corrosion resistant sealing material that has defined therein one, preferably at least two, and more preferably a plurality (e.g., the number N as defined previously) of gasket holes. Examples of such material are polymer, interpolymer, and cork. The at least two gasket holes align with, and are in fluid communication with, at least two of test holes in a test framework (e.g., 33). A gasket hole provides a test liquid access to directly contact test areas of a first or second test coupon (e.g., 32 and 34) and helps prevent test liquids in different test chambers (e.g., 55, not indicated) from fluidly communicating with one another. A first and second sealing means 2 (not shown) may comprise one gasket comprised of one contiguous material that wraps around a side of a test framework so that a portion of the gasket seals a bottom face of the test framework and another portion of the gasket seals a top face of the test framework. A gasket may or may not have a ridge surrounding a gasket hole and complimentary-shaped to a flanged hole in a test framework. Such a ridge would function in a manner analogous to an O-ring, which is a circular-shaped material comprised of any chemical and corrosion resistant sealing material.

Typically, an O-ring or gasket material is a polymer or interpolymer such as, for example, a fluoroelastomer, perfluoroelastomer (PFE), acrylonitrile butadiene rubber, a polysiloxane, ethylene propylene diene monomer rubber, polychloroprene elastomer, a polyurethane, PTFE, and fluorinated ethylene propylene. Preferably, an O-ring is seated on a flange formed in the test framework at an opening in a face of the test framework. Two or more different types of sealing means 2 (not shown) may be used in an invention apparatus or method or as a first or second sealing means 2 (not shown). Preferably a sealing means 2 (not shown) is an O-ring or gasket, more preferably an O-ring.

In another embodiment, the invention apparatus (e.g., 10 in FIG. 1) of the first embodiment further comprises a securing means 4 (not indicated), which operatively contacts the bottom face (e.g., 12a) of the first test coupon (e.g., 32) and the top face (e.g., 14b) of the second test coupon (e.g., 34) and is for securing test liquids in the at least two test chambers 55

(not indicated) against fluid communication with each other. A "securing means" refers to any device for securing an assembly comprising a first test coupon (e.g., 32), test framework (e.g., 33), second test coupon (e.g., 34), and, optionally, first and second sealing means 2 (e.g., 24 and 26), against separating during an invention method, wherein the separating undesirably allows test chambers (e.g., 55, not indicated) to fluidly communicate with each other (i.e., with one another). Thus, a securing means 4 (not shown) includes devices for securing an apparatus (e.g., 10 in FIG. 1) comprising a first backing means (e.g., 31*a*), first test coupon (e.g., 32), test framework (e.g., 33), second test coupon (e.g., 34), second backing means (e.g., 31*b*), and, optionally, first and second sealing means 2 (e.g., 24 and 26), against separating during an invention method. A securing means 4 (not shown) may be any shape. Two or more securing means 4 (not shown) may be comprised of the same or different material. A securing means 4 (not shown) may be comprised of any material such as, for example, wood, metal, polymer, interpolymer, glass, and ceramic.

Examples of securing means 4 (not shown) are a clamp, frame, stretchable band (e.g., rubber band) or cord (e.g., rubber cord), closable container (into which the assembly is placed), and fastening means 6 (all not shown). A fastening means 6 (not shown) comprises at least one alignable, internally screw-threaded, fastening hole (e.g., 28*a*) and at least one externally screw-threaded fastener (94, not shown), which operates with the at least one alignable, internally screw-threaded, fastening hole (e.g., 28*a*) to apply a securing force (e.g., in the direction indicated by arrow 27*a*), which is preferably a compression force, to operatively secure a test coupon (e.g., 32) to a test framework (e.g., 33). In response to a compression force applied from a securing means 4 (not shown), a test hole (e.g., 25) may slightly deform to an irregular shape, which may desirably enhance mixing of an agitated test liquid in the test hole (e.g., 25). Optionally, there is at least one internally screw-threaded fastening hole (e.g., 85, not indicated) in the test framework (e.g., 33). When an externally screw-threaded fastener (e.g., 92, not shown) having a head and a tip is inserted tip first into the test framework (e.g., 33), the tip may or may not protrude out of the test framework (e.g., 33). A particular externally screw-threaded fastener (e.g., 92, not shown) may be inserted through one test coupon (e.g., 32), each test coupon (e.g., 32 and 34), or no test coupon. Optionally, when an invention apparatus (e.g., 10 of FIG. 1) comprises one or two backing means (e.g., 31*a* or 31*a* and 31*b*, respectively), each externally screw-threaded fastener (e.g., 92 and 94, all not shown) independently may be inserted through one backing means (e.g., 31*a*), each backing means (e.g., 31*a* and 31*b*), or no backing means.

A combination of different securing means 4 (not shown) may be used. For example, a test framework (e.g., 33) may also function as a securing means 4 (not shown) for a first coupon (e.g., 32), as described previously, and another securing means 4 (not shown, i.e., not the test framework, e.g., 33) may be employed to secure the second metal test coupon (e.g., 34). Another example of a combination of different securing means 4 (not shown) is a combination of a fastening means 6 (not shown) and a clamp (not shown), which may be employed together.

A securing means 4 (not shown) may secure an invention apparatus assembly (e.g., 10 in FIG. 1) by applying a force (e.g., in direction indicated by arrow 27*a*), via direct or indirect contact, to a bottom face (e.g., 12*a*) of the first test coupon (e.g., 32) and a (counter direction) force (e.g., in direction indicated by arrow 27*b*), via direct or indirect contact, to a top face (e.g., 14*b*) of the second test coupon (e.g., 34). Any type of force may be employed. Examples of such forces are a compressing force (e.g., via a clamp, frame, or fastening means 6 (not shown)), adhesive force, magnetic force, or a combination thereof. A force may be applied by direct or indirect physical contact between a securing means 4 (not shown) and a test coupon (e.g., 32 and 34).

In another embodiment, the invention apparatus of the first embodiment (e.g., 10 in FIG. 1) further comprises a first backing means (e.g., 31*a*), second backing means (e.g., 31*b*), and a securing means 4 (not shown); wherein each of the first and second backing means independently comprises a top face (e.g., 11*b* and 15*b*, respectively) and a bottom face (e.g., 11*a* and 15*a*, respectively) that is generally flat and spaced apart from, and generally parallel to, the other; the first backing means (e.g., 31*a*) may be disposed between the first test coupon (e.g., 32) and the securing means (not indicated) so that the top face (e.g., 11*b*) of the first backing means (e.g., 31*a*) operatively contacts the bottom face (e.g., 12*a*) of the first test coupon (e.g., 32) and the bottom face (e.g., 11*a*) of the first backing means (e.g., 31*a*) operatively contacts the securing means 4 (not shown); the second backing means (e.g., 31*b*) may be disposed between the second test coupon (e.g., 34) and the securing means 4 (not shown) so that the bottom face (e.g., 15*a*) of the second backing means (e.g., 34) operatively contacts the top face (e.g., 14*b*) of the second test coupon (e.g., 34) and the top face (e.g., 15*b*) of the second backing means (e.g., 31*b*) operatively contacts the securing means 4 (not shown), wherein the first and second backing means (e.g., 31*a* and 31*b*) and securing means 4 (not shown) are for securing test liquids in the at least two test chambers (e.g., 55, not indicated) against fluid communication with each other.

A "backing means" (e.g., 31*a* and 31*b*) refers to any device that operates with a securing means 4 (not shown) to compress a test coupon (e.g., 32) and a test framework (e.g., 33) together. A backing means (e.g., 31*a* and 31*b*) may take any shape such as a plate or block and may be comprised of any material such as, for example, wood, metal, polymer or interpolymer (e.g., copolymer, terpolymer, etc.), glass, and ceramic. Preferably, a backing means (e.g., 31*a* and 31*b*) comprises at least one face (e.g., 11*b* and 15*a*) that is generally flat. In some embodiments, a backing means (e.g., 31*a* and 31*b*) comprises a top face (e.g., 11*b* and 15*b*, respectively) and a bottom face (e.g., 11*a* and 15*a*, respectively) that are generally flat and spaced apart from, and generally parallel to, each other. Preferably, such a face (e.g., 11*b*) of a backing means (e.g., 31*a*) is in operative contact with a bottom face (e.g., 12*a*) of a test coupon (e.g., 32) and the other such face (e.g., 11*a*) of the backing means (e.g., 31*a*) is in operative contact with a securing means 4 (not shown). In other embodiments, preferably a backing means (e.g., 31*a* and 31*b*) comprises at least one face (e.g., 11*b* and 15*a*) that is generally flat and another face (not shown) that is contoured and spaced apart from the generally flat face. In still other embodiments, a backing means (not shown) comprises top and bottom faces (not shown) that are each independently contoured (e.g., dimpled, not shown), preferably uniformly contoured (e.g., a plurality of uniformly sized and spaced apart dimples, not shown). The contoured face (not shown) of such backing means (not shown) that engages a securing means 4 (not shown) may be any shape and may include structural features for attaching a securing means thereto such as, for example, hooks, latches, loops, holes, and knobs (all not shown). First and second backing means (e.g., 31*a* and 31*b*) may be comprised of the same or different material.

A first and second backing means (e.g., 31*a* and 31*b*) and a securing means 4 (not shown) may be integrated in a unified backing and securing means 4 (not shown). Examples of a unified backing and securing means are a C-shaped clamp, closable container (dimensioned for containing an assembly of a first and second test coupon (e.g., 32 and 34), first and second sealing means 2 (e.g., 24 and 26) and test framework (e.g., 33), and a vise holder in a mechanical agitation (e.g., rocker) apparatus (all not shown).

The term "test liquid" is any mixture comprising at least an electrolytic solution, which typically comprises water and an electrolyte (e.g., inorganic salt) dissolved therein. As described below, the test liquid may further comprise one or more additives desired for modulating effects of corrosion testing. Less preferably, any invention method may alternatively employ one or more test liquids comprising deionized water and the one or more additional components (i.e., a test liquid wherein there is no electrolyte dissolved therein). An electrolytic solution supports electrolysis and is a solution comprised of water and at least one electrolyte (e.g., an inorganic salt). Salt water, i.e., a solution of sodium chloride (NaCl) in water, is an example of an electrolytic solution. Examples of water are $H_2O$ and $D_2O$, deionized water and distilled water. A composition of any particular test liquid is independently chosen without regard to a composition of any other test liquid. A test liquid may be comprised of one or more phases. Phases of test liquids include one, two or more phase solutions, emulsions, and suspensions of solids in solutions or emulsions. Physico-chemical properties of electrolytic solutions may be varied by varying components, absolute or relative concentrations of electrolytes or additives, varying pH, varying the atmosphere (e.g., air and pure oxygen gas) that is in direct contact with the electrolytic solutions, and varying temperature.

Test liquids may further comprise additives such as, for example, antioxidants, buffers, corrosion inhibitors, corrosion enhancers, emulsifiers, lubricity aids, lubricant formulations, and formulation stabilizers. Examples of lubricant formulations are ship stern lubricants, bearing lubricants, mill and calendar lubricants, high temperature lubricants, food grade lubricants, textile machine lubricants, greases and solid lubricant dispersions, compressor lubricants, coating fluids (e.g., for brake parts), refrigeration lubricants, 2-cycle engine oil lubricants, motor oils, machinery lubricants, transmission fluids, aircraft deicing fluids, paints, and coatings such as I-beam coatings. Examples of lubricant materials are polyalkylene glycols (PAGs), polyfluoroalkyl polyethers (PFPE), polyphenyl ethers, polysiloxanes, polyphosphate esters, polyalphaolefins (PAOs), diesters and polyol esters, plant-derived biolubricants, and mineral oils. Examples of suitable corrosion enhancers are organic acids, inorganic acids, microbes, ligands to metals, and oxidants such as, for example, peroxides, oxygen, and inorganic oxidizing reagents.

In an invention method, a test liquid in a test chamber (not indicated) is present in a corrosion testing amount. The term "corrosion testing amount" means that a volume of a test liquid in a test chamber (not indicated) is sufficient for the test liquid to simultaneously contact at least a portion of the relevant separate test area (not indicated) circumscribed on the top face (e.g., 12b) of the first test coupon (e.g., 32) and at least a portion of the relevant separate test area (not indicated) circumscribed on the bottom face (e.g., 14a) of the second test coupon (e.g., 34) and comprise a contiguous liquid phase between the relevant test areas (not indicated) so that the relevant test areas (not indicated) are in electrolytic communication (i.e., able to participate in a voltaic corrosion process) with each other. All other things being equal and assuming test liquids in an invention apparatus (e.g., 10 of FIG. 1) are not agitated, a corrosion testing amount for when an invention apparatus (e.g., 10 of FIG. 1) is laid on its side (not indicated) so that test holes (e.g., 25) in a test framework (e.g., 33) of the invention apparatus (e.g., 10 of FIG. 1) are horizontally oriented will be lower than a corrosion testing amount for a when the invention apparatus (e.g., 10 of FIG. 1) is laid flat so that the test holes (e.g., 25) in the test framework (e.g., 33) are vertically oriented (e.g., as depicted for 25 in FIG. 1).

In a method of the invention, test liquids in reaction chambers (not indicated) of an invention apparatus (e.g., 10 of FIG. 1) may or may not be agitated. Test liquids may be agitated by any conventional means. Examples of agitating by conventional means (not shown) are mechanically rocking, rotating, shaking, bouncing, and spinning the invention apparatus (e.g., 10 of FIG. 1). Other means of agitating test liquids in reaction chambers (not indicated) of an invention apparatus (e.g., 10 of FIG. 1) are contemplated such as, for example, placing stir bars (not shown) in the reaction chambers (not shown) and placing the invention apparatus (e.g., 10 of FIG. 1) on a multiple stirrer assembly (not shown). In some embodiments, test liquids are not agitated during an invention method. In other embodiments, test liquids are agitated during an invention method. Agitating a test liquid facilitates contacting in a test chamber the test liquid to an entire test area (not indicated) of the first test coupon (e.g., 32), second test coupon (e.g., 34), or preferably both (e.g., 32 and 34). In some embodiments, an invention method further comprises the step of agitating the at least two test liquids.

The term "operatively contacts" refers to a direct (i.e., there is/are no intermediary component(s), e.g., such as between first backing means 31a and first test coupon 32)) or indirect (i.e., there is an intermediary component(s), e.g., such as between first backing means 31a and test framework 33, wherein the intermediary components are first test coupon 32, sealing means 24, or both) physical contact, e.g., between two objects and allows the two objects to function in a method of the invention. An example of indirect physical contact is a test framework (e.g., 33) and test coupon (e.g., 32 and 34) that are spaced apart from each other, but placed in sealing connection with each other by, via, for example, a sealing means 2 (e.g., 24 and 26, respectively), which is disposed between the test framework (e.g., 33) and the test coupon (e.g., 32 and 34). In some embodiments, a sealing means 2 (e.g., 24 and 26) operatively contacts at least a sealing surface portion (not indicated) of a test coupon (e.g., 32 and 34) and at least a sealing surface portion (not indicated) of a test framework (e.g., 33) as described previously so that the test coupon (e.g., 32 and 34) and test framework (e.g., 33) are spaced apart from, and do not directly contact, each other. In other embodiments, a sealing means 2 (e.g., 24 and 26) operatively contacts at least a sealing surface portion (not indicated) of a test coupon (e.g., 32 and 34) and at least a sealing surface portion (not indicated) of a test framework (e.g., 33) and the test coupon (e.g., 32 and 34) and test framework (e.g., 33) directly contact each other, either at spots (not indicated) or across entire faces (e.g., 12b and 13a and 14a and 13b). A "sealing contact" prevents fluid communication between test chambers (e.g., 55, not indicated).

A "face" (e.g., 12a and 12b) refers to a presenting surface. Preferably the presenting surface (e.g., 12a and 12b) is complimentary-shaped to an object such as a sealing means 2 (e.g., 24 and 26) where the presenting surface (e.g., 12a and 12b) directly contacts (i.e., touches) the object. Preferably, any two directly contacting faces (e.g., 12b and 11b) make a face-to-face, preferably flush, physical contact. The invention apparatus, however, includes embodiments comprising an additional intermediary material that is disposed between two engaging faces (e.g., 12a and 11b) of a test coupon (e.g., 32) and backing means (e.g., 31a), or backing means (e.g., 31a) and securing means 2 (not shown). Examples of such intermediary material include an adhesive, lubricant, gasket, and cloth.

The phrases "fluid communication" and "in fluid communication" refer to a capability for allowing movement of a test liquid such as movement, for example, from one test chamber (not indicated) to another test chamber (not indicated) or within a test chamber (not indicated) between opposing test areas (not indicated) of first and second test coupons (e.g., 32 and 34).

The words of "first," "second," etc., when used to distinguish embodiments or components (e.g., test coupons (e.g., 32 and 34) and backing means (e.g., 31a and 31b)) of the invention apparatus (e.g., 10 of FIG. 1) or method, are used for convenience and do not imply any particular quantity, order or priority unless specifically stated otherwise. Likewise, the words "top" and bottom," when used to distinguish elements or steps of the invention, are used for convenience and do not imply any particular required orientation with respect to a vertical or horizontal plane.

The phrase "may be the same or different" indicates identical type or non-identical type, respectively.

Examples of suitable polymers and interpolymers useful for backing means, sealing means 2 (not shown), securing means, or test framework are found in "Polymer Handbook", 4$^{th}$ Ed, Brandrup, Immergut, and Grulke, Eds., Wiley, 1999; and "Copolymerization", G. E. Ham, Ed., *High Polymers*, Vol. XVIII, Interscience, 1964.

The invention apparatus (e.g., 10 of FIG. 1) may be used for testing voltaic corrosion. Voltaic corrosion occurs when two dissimilar electrical conductors (e.g., test coupons 32 and 34) are in contact with one and the same electrolytic solution and passive degradation of at least one of the conductors occurs. Electrochemical corrosion occurs when two identical electrical conductors (e.g., each identical steels compositions, or two dissimilar electrical conductors (e.g., test coupons 32 and 34), are immersed in one and the same electrolytic solution and a voltage is applied across the conductors (e.g., test coupons 32 and 34) that actively facilitates or enhances degradation of at least one of the conductors (e.g., test coupons 32 and 34).

The phrase "voltaic couple" refers to two dissimilar electrical conducting (e.g., test coupons 32 and 34). A voltaic couple may also be referred to as a passive galvanic couple. Two dissimilar electrical conducting metals may be selected in view of where they fall in a galvanic series, which relates to a measure of electropotential between two metals under voltaic or electrochemical corrosion test conditions. Orders of metals may differ in galvanic series depending on oxygen content of an electrolytic solution used to measure electropotential. When measured in salt water having a low (e.g., less than 1 mole %) oxygen content, the following galvanic series is observed in order of increasing susceptibility to galvanic corrosion:
graphite<palladium<platinum<gold<silver<titanium<stainless (carbon) steel (316, passive corrosion protection conditions) <stainless (carbon) steel (304, passive corrosion protection conditions)<silicon bronze<stainless (carbon) steel (316 active corrosion protection conditions)<Alloy 400 (a nickel-copper alloy)<phosphor bronze<admiralty brass<cupronickel<molybdenum<red brass<brass plating<yellow brass<naval brass 464<uranium 8% Mo<niobium 1% Zr<tungsten<stainless (carbon) steel (304 active corrosion protection conditions)<tantalum<chromium plating<nickel (passive corrosion protection conditions) <copper<nickel (active corrosion protection conditions) <cast iron<carbon steel<lead<tin<indium<aluminum<uranium (pure) <cadmium<beryllium<zinc plating<magnesium.

The term "analyzing" refers to examining a test coupon (e.g., 32 and 34) having a test area (not indicated) on a face (e.g., 12b and 14a, respectively) that has been exposed to a test liquid. Evidence of corrosion includes, for example, visual evidence (e.g., see FIG. 2), physical evidence, and chemical evidence. Examples of visual evidence of corrosion are pitting, cracking, etching, and discoloration, or any combination thereof of the face of the test coupon. Examples of physical evidence include a change in weight of the test coupon (e.g., 32 and 34), which may be determined by weighing the test coupon (e.g., 32 and 34) at the start of and near the end of the method. Examples of chemical evidence of corrosion are chemical analysis of a sample scraped from the face (e.g., 12b and 14a) of the test coupon (e.g., 32 and 34, respectively) or spectrochemical analysis of the surface.

The invention apparatus (e.g., 10 in FIG. 1) may also be used for active galvanic corrosion testing of first and second test coupons that are first and second metal test coupons (e.g., 32 and 34), respectively. Accordingly, a third embodiment of the invention is a method comprising: providing an apparatus according to claim 1 and a corrosion testing amount of a test liquid in each one of the at least two test chambers (e.g., 55, not indicated), wherein the test liquids in the at least two test chambers (e.g., 55, not indicated) may be the same or different and are secured against fluid communication with each other, and the first and second test coupons are first and second metal test coupons, respectively; applying a voltage across the first and second metal test coupons; and analyzing at least one of the first and second metal test coupons for corrosion.

The invention apparatus (e.g., 10 in FIG. 1) may also be used for electroplating testing. Evidence of electroplating includes, for example, visual evidence, physical evidence, and chemical evidence. Examples of visual evidence of corrosion are changes in coloration or light reflecting properties, or any combination thereof of a face (e.g., 12b) of a test coupon (e.g., 32). Examples of physical evidence include a change in weight of the test coupon (e.g., 32), which may be determined as described above. Examples of chemical evidence of electroplating are chemical analysis of a sample scraped from the face (e.g., 12b) of the test coupon (e.g., 32) or spectrochemical analysis of the surface (not indicated) of the face (e.g., 12b). Thus, a fourth embodiment of the invention is a method comprising: providing an apparatus according to claim 1 and a electroplating amount of a test liquid in each one of the at least two test chambers (e.g., 55, not indicated), wherein the test liquids in the at least two test chambers (e.g., 55, not indicated) may be the same or different and are secured against fluid communication with each other and the first and second test coupons are first and second metal test coupons, respectively; applying a voltage across the first and second metal test coupons; and analyzing at least one of the first and second metal test coupons for deposited metal.

Examples 1 and 2 below illustrate application of the invention apparatus and method to high throughput, voltaic corrosion testing for discovering improved combinations of industrial fluids.

Example 1

Industrial fluids containing a mixture of propylene glycol and water thickened with partially neutralized polyacrylic acid, and further containing surfactant, anti-corrosion additives, and dye are tested for discoloration of carbon steel coupon, Society of Automotive Engineers (SAE) Standard 1020 (e.g., 132). Industrial fluid formulations 196, 205, and 206 are used for calibration. Calibration formulation 196 is known to be non-discoloring and calibration formulation 205 is known to be discoloring from previous corrosion testing. Calibration formulation 206 is expected to be slightly discoloring based on its composition.

Corrosion test procedure: employing invention apparatus 100 having disposed therein ninety-six test chambers 155 as described previously. Test chambers 155 are arranged in a grid comprised of 8 rows A to H and 12 columns 1 to 12 and located, for convenience, in the grid by row and column number as being at: A1 to A12, B1 to B12, C1 to C12, D1 to D12, E1 to E12, F1 to F12, G1 to G12, and H1 to H12. Steel coupon (e.g., 132) is washed with soap and water, rinsed with distilled water and ethanol, and dried under a stream of nitrogen gas. The washed steel coupon (e.g., 132), a first aluminum plate (e.g., 131a), 96 O-rings (e.g., 124), and a PEEK test framework (e.g., 133) are assembled and secured together by finger tightening a total of 9 bottom screws (e.g., one center fastener 192 and eight perimeter fasteners 194) until the 9 bottom screws are evenly tightened. The resulting bottom assembly (comprising first aluminum plate, e.g., 131a; steel coupon, e.g., 132; 96 O-rings, e.g., 124; and test framework, e.g., 133; and the 9 bottom screws (e.g., one center fastener 192 and eight perimeter fasteners 194) is then checked for proper alignment and tight seals. (All not shown.)

Corrosion testing amounts of calibration formulations 196, 205, and 206 are placed in test holes (e.g., 125) D2 to D6, F2 to F6, and B2 to B6, respectively, as described above, and the remaining test holes (e.g., 125) are left empty. To the bottom assembly (comprising first aluminum plate, e.g., 131a; steel coupon, e.g., 132; 96 O-rings, e.g., 124; and test framework, e.g., 133; and the 9 bottom screws (e.g., one center fastener 192 and eight perimeter fasteners 194)) containing the formulations described above are assembled and secured together an additional 96 O-rings (e.g., 126), a copper coupon (e.g., 134) and a second aluminum plate (e.g., 131b) by finger tightening nine top screws (e.g., one center fastener 192 and eight perimeter fasteners 194). Thus, the resulting assembled invention apparatus (e.g., 100) contains a total of 15 test calibration formulations. The invention apparatus (e.g., 100) is placed flat on a bottom face (e.g., 111a) of the first aluminum plate (e.g., 131a) in an air oven set at 50° C. for 24 hours, removed, and allowed to cool to room temperature. (All not shown.)

After the apparatus is cooled to room temperature, the invention apparatus (e.g., 100) is disassembled to give the bottom assembly described previously, and the calibration formulations are poured out of their test holes (e.g., 125). The PEEK test framework (e.g., 133) is removed from the steel coupon (e.g., 132). Any stuck O-rings (e.g., 124) are dislodged from the steel coupon (e.g., 132) and residual calibration formulations are rinsed from the steel coupon (e.g., 132) with water. The steel coupon (e.g., 132) is dried under a nitrogen stream and may be digitally imaged as described below in Example 3. Since the invention apparatus (e.g., 100) is placed flat on a bottom face (e.g., 111a) of the first aluminum plate (e.g., 131a), it is likely in this experiment that each calibration formulation has only been in contact with portions (not indicated) of the exposed (to test liquid) test areas (e.g., 146) of the copper coupon (e.g., 134) and not with the entire test areas (e.g., 146) of the copper coupon (e.g., 134) in test chambers (e.g., 155). Accordingly, the copper coupon (e.g., 134) is not digitally imaged, but is visually inspected for evidence of corrosion. Calibration formulation 196 causes essentially no discoloration of steel coupon (e.g., 132) while calibration formulation 205 causes a dark, black discoloration of the steel coupon (e.g., 132). Calibration formulation 206 causes mild to no discoloration of steel coupon (e.g., 132). (All not shown).

Example 2

Eight test formulations 262 to 264 and 270 to 274 are prepared. Test formulations 262 to 264 and 270 to 274 each contain propylene glycol, water, polyacrylic acid, surfactant, sodium tolyltriazole, and dye in the same proportions and, further, independently contain sodium hydroxide (NaOH), potassium dihydrogen phosphate ($KH_2PO_4$), and/or potassium sorbate ($CH_3CH$=$CHCH$=$CHCO_2K$) in the proportions shown in Table 1.

TABLE 1

| Formu-lation | Weight % | | | pH | Degree of Discoloration |
| --- | --- | --- | --- | --- | --- |
| | NaOH | KH2PO4 | Potassium Sorbate | | |
| 262 | 0.107 | 0.147 | 0.100 | 7.27 | severe |
| 263 | 0.106 | 0.147 | 0.300 | 7.20 | severe |
| 264 | 0.106 | 0.146 | 0.513 | Not measured | severe |
| 270 | 0.075 | 0 | 0.101 | 7.00 | mild |
| 271 | 0.075 | 0.050 | 0.100 | 6.87 | moderate |
| 272 | 0.075 | 0 | 0.201 | 6.92 | mild |
| 273 | 0.075 | 0 | 0.251 | 6.93 | mild |
| 274 | 0.074 | 0.099 | 0.100 | 6.84 | severe |

In a manner similar to that described for Example 1, an invention apparatus (e.g., 100) is assembled in a manner similar to that described for Example 1, wherein corrosion testing amounts of test formulation 262 are sealed in test holes (e.g., 125) A1 to A6; corrosion testing amounts of test formulation 263 are sealed in test holes (e.g., 125) B1 to B5; corrosion testing amounts of test formulation 264 are sealed in test holes (e.g., 125) C1 to C4; corrosion testing amounts of test formulation 270 are sealed in test holes (e.g., 125) D1 to D6; corrosion testing amounts of test formulation 271 are sealed in test holes (e.g., 125) E1 to E6; corrosion testing amounts of test formulation 272 are sealed in test holes (e.g., 125) F1 to F6; corrosion testing amounts of test formulation 273 are sealed in test holes (e.g., 125) G1 to G6; corrosion testing amounts of test formulation 274 are sealed in test holes (e.g., 125) H1 to H6; corrosion testing amounts of calibration formulation 206 are sealed in test holes (e.g., 125) B9 to B11; corrosion testing amounts of calibration formulation 196 are sealed in test holes (e.g., 125) C9 to C11; and corrosion testing amounts of calibration formulation 205 are sealed in test holes (e.g., 125) D9 to D11. The apparatus (e.g., 100) is held at 50° C. for 24 hours. FIG. 2 shows the top face (e.g., 112b) of the steel coupon (e.g., 132) from this corrosion test. Calibration formulations 206, 196, and 205 give discoloration results on the steel coupon (e.g., 132) similar to those of Example 1. Test formulations 262, 263, 264, and 274 give severe discoloration, test formulation 271 gives moderate discoloration, and test formulations 270, 272, and 273 give mild discoloration on the steel coupon (e.g., 132). As indicated in Table 1, the three test formulations which mildly discolor the steel coupon (e.g., 132) contain no phosphate and the five test formulations that severely or moderately discolor the steel coupon (e.g., 132) contain phosphate, demonstrating that phosphate is a source of the discoloration of the steel coupon (e.g., 132). (All not shown).

Example 3 below generally illustrates a method of digitally analyzing a test area (not indicated) of a top face (e.g., 112b) of a test steel coupon (e.g., 132) for evidence of corrosion. (All not shown).

Example 3

Corrosion Imaging and Analysis

A plurality of corrosion tests on a steel coupon (e.g., 132) are carried out in a manner similar to that described for Example 1 or 2, for example. Digital photographs of the steel coupon (e.g., 132) are taken with a digital camera (e.g., a Nikon Coolpix 5700 digital camera) and stored in a computer. The stored image is processed using ImageJ image processing software (shareware) residing on the computer, and the processed images are preferably displayed on a color digital display. The processed images may be displayed, printed, stored electronically, or any combination thereof as gray scale or color images.

The ImageJ software is used to determine gray-scale values or color density values, respectively, for the images. For each corrosion test image, a region of interest (test ROI) within a test area (not indicated) of a corrosion test image and a ROI (reference ROI) within a nearby (to the test ROI) corrosion-free, non-test area (i.e., area between two or more corrosion test areas) of the steel coupon (e.g., 132) are delineated. For black-and-white analysis of the ROIs, a digital gray scale reading is taken in each reference ROI to give a background reference value. Separately, a digital gray scale reading is taken in the test ROI to give an experimental value. A ratio of the experimental gray scale value divided by the reference gray scale value for each different test liquid is determined in order to compare results between different corrosion tests. For the ratios, a number nearer 1 indicates little discoloration (i.e., little corrosion) whereas a number nearer 0 indicates significant discoloration (i.e., significant corrosion). For color analysis of the ROIs, a color density value is separately determined for a test ROI and its reference ROI, and the resulting experimental and reference color density values are compared to each other to determine a degree of corrosion in the test ROI.

The method of Example 3 may be readily adapted for analyzing a top face (e.g., 112b) of a test coupon (e.g., 132) for evidence of electroplating.

All references herein to a Periodic Table of the Elements shall refer to the Periodic Table of the Elements published and copyrighted by CRC Press, Inc., 2003. Also, any references to an atomic number of a chemical element shall be to the atomic number reflected in this Periodic Table of the Elements using the IUPAC system for numbering groups disclosed in, *Nomenclature of Inorganic Chemistry: Recommendations 1990*, G. J. Leigh, Editor, Blackwell Scientific Publications (1990).

Examples of objects, materials, characteristics, and features are listed herein for illustration purposes and are non-limiting. A non-listed conventional object, material, characteristic, or feature may be substituted for a listed one.

Example(s) of the invention and Preparation(s), if any, described herein are for illustration purposes. Using methods analogous to those described therein, it is possible to prepare or conduct any embodiment of the invention without undue experimentation.

All invention elements and limitations comprising any embodiment of the invention are independently selected unless otherwise specified. All journal articles, text books, patents, published patent applications, and unpublished patent applications referenced herein are hereby incorporated by reference in their entireties for any and all purposes.

Illustrative embodiments of the invention are described herein. One of ordinary skill in the art (artisan) would know that supportable changes and modifications may be made to these embodiments without departing from the metes and bounds of the invention as described or claimed herein. Such supportable changes and modifications include substituting the phrase "consisting essentially of" or the phrase "consisting of" for any or all occurrences of the term "comprising" used in the description, including the claims.

What is claimed is:

1. An apparatus comprising:
   (a) a first test coupon, which comprises a top face and a bottom face;
   (b) a test framework, which comprises a top face, bottom face, and a plurality of walls that define a number N of test holes; wherein the top and bottom faces of the test framework are generally flat, spaced apart from, and generally parallel to, each other; the test holes pass through the test framework between bottom openings at the bottom face of the test framework and top openings at the top face of the test framework and are spaced apart from each other; N is an integer of from 2 to 200; and the bottom face of the test framework operatively contacts, around the bottom openings of at least two of the test holes, the top face of the first test coupon to independently circumscribe at least two separate test areas on the top face of the first test coupon; and
   (c) a second test coupon, which comprises a top face and a bottom face; wherein the top face of the test framework operatively contacts, around the top openings of the at least two test holes, the bottom face of the second test coupon to independently circumscribe at least two separate test areas on the bottom face of the second test coupon;
   wherein at least two test chambers are defined by the walls of the at least two test holes, the at least two separate test areas circumscribed on the top face of the first test coupon, and the at least two separate test areas circumscribed on the bottom face of the second test coupon.

2. The apparatus according to claim 1, the apparatus further comprising a securing means, which operatively contacts the bottom face of the first test coupon and the top face of the second test coupon.

3. The apparatus according to claim 1, the apparatus further comprising a first backing means, a second backing means, and a securing means; wherein the first backing means independently comprises a top face and a bottom face that is generally flat and spaced apart from, and generally parallel to, each other; the second backing means independently comprises a top face and a bottom face that is generally flat and spaced apart from, and generally parallel to, the other; the first backing means is disposed between the first test coupon and the securing means so that the top face of the first backing means operatively contacts the bottom face of the first test coupon and the bottom face of the first backing means operatively contacts the securing means; the second backing means is disposed between the second test coupon and the securing means so that the bottom face of the second backing means operatively contacts the top face of the second test coupon and the top face of the second backing means operatively contacts the securing means.

4. The apparatus according to claim 1, the apparatus further comprising at least one sealing means, which either is disposed between, and forms a sealing contact with, the top face of the first test coupon and the bottom face of the test framework around a bottom opening of one of the at least two test holes or is disposed between, and forms a sealing contact with, the bottom face of the second test coupon and the top face of the test framework around a top opening of the same one of the at least two test holes.

5. The apparatus according to claim 4, wherein the sealing means independently comprises a gasket or an O-ring.

6. The apparatus according to claim 1, wherein the first test coupon is a first metal test coupon comprising palladium, platinum, gold, silver, titanium, stainless steel, silicon, brass, tungsten, tantalum, chromium, nickel, copper, carbon steel, lead, tin, aluminum, or zinc.

7. The apparatus according to claim 6, wherein the second test coupon comprises a second metal test coupon comprising palladium, platinum, gold, silver, titanium, stainless steel, silicon, brass, tungsten, tantalum, chromium, nickel, copper, carbon steel, lead, tin, aluminum, or zinc.

8. The apparatus according to claim 1, wherein the test framework is comprised of a polymer-or interpolymer-based chemical and corrosion resistant structural material.

9. The apparatus according to claim 1, wherein the first and second test coupons are first and second metal test coupons, respectively, and the first and second metal test coupons comprise a voltaic couple.

10. A method comprising the steps of:
(a) providing an apparatus comprising:
(i) a first test coupon, which comprises a top face and a bottom face;
(ii) a test framework, which comprises a top face, bottom face, and a plurality of walls that define a number N of test holes; wherein the top and bottom faces of the test framework are generally flat, spaced apart from, and generally parallel to, each other; the test holes pass through the test framework between bottom openings at the bottom face of the test framework and top openings at the top face of the test framework and are spaced apart from each other; N is an integer of from 2 to 200; and the bottom face of the test framework operatively contacts, around the bottom openings of at least two of the test holes, the top face of the first test coupon to independently circumscribe at least two separate test areas on the top face of the first test coupon; and
(iii) a second test coupon, which comprises a top face and a bottom face; wherein the top face of the test framework operatively contacts, around the top openings of the at least two test holes, the bottom face of the second test coupon to independently circumscribe at least two separate test areas on the bottom face of the second test coupon;
wherein at least two test chambers are defined by the walls of the at least two test holes, the at least two separate test areas circumscribed on the top face of the first test coupon, and the at least two separate test areas circumscribed on the bottom face of the second test coupon;
(b) contacting a corrosion testing amount of a test liquid in each one of the at least two test chambers to at least one of the first and second test coupons, wherein the test liquids in the at least two test chambers may be the same or different and are secured against fluid communication with each other; and
(c) analyzing at least one of the first and second test coupons for corrosion.

* * * * *